United States Patent [19]

Finch et al.

[11] Patent Number: 4,908,386
[45] Date of Patent: Mar. 13, 1990

[54] ETHANOLAMINE DERIVATIVES

[75] Inventors: Harry Finch, Hitchin; Lawrence H. C. Lunts, Broxbourne; Alan Naylor, Royston; Ian F. Skidmore, Welwyn; Ian B. Campbell, Ware; David Middlemiss; Charles Willbe, both of Bishops Stortford, all of England

[73] Assignee: Glaxo Group Limited, London, England

[21] Appl. No.: 287,441

[22] Filed: Dec. 20, 1988

Related U.S. Application Data

[63] Continuation of Ser. No. 919,123, Oct. 15, 1986.

[30] Foreign Application Priority Data

Oct. 15, 1985 [GB] United Kingdom ............... 8525478
Oct. 15, 1985 [GB] United Kingdom ............... 8525479
Oct. 15, 1985 [GB] United Kingdom ............... 8525480
Oct. 15, 1985 [GB] United Kingdom ............... 8525481
Oct. 15, 1985 [GB] United Kingdom ............... 8525485

[51] Int. Cl.⁴ .................... C07C 143/74; A61K 31/18
[52] U.S. Cl. ..................................... 514/605; 514/255; 514/330; 514/331; 514/423; 514/428; 514/456; 514/466; 514/484; 514/487; 514/522; 514/523; 514/524; 514/539; 514/562; 514/563; 514/564; 514/565; 514/595; 514/597; 514/600; 514/629; 514/649; 514/651; 514/718; 514/826; 514/227.5; 514/227.8; 514/231.2; 514/235.5; 514/239.5; 544/59; 544/159; 544/165; 544/398; 544/400; 546/221; 546/226; 546/232; 546/233; 546/234; 548/567; 548/569; 548/577; 549/365; 549/441; 549/443; 549/408; 558/408; 558/413; 558/414; 558/422; 560/13; 560/27; 560/34; 560/42; 562/430; 562/434; 562/452; 564/49; 564/50; 564/51; 564/56; 564/79; 564/99; 564/220; 564/363; 564/369

[58] Field of Search ...................... 548/577, 567, 569; 546/234, 232, 221, 226, 233; 514/826, 651, 649, 718; 564/363, 369; 544/59, 159, 165, 348, 400, 365, 441, 443, 444; 558/408, 413, 414, 422

[56] References Cited

U.S. PATENT DOCUMENTS

| 3,818,101 | 6/1974 | Baile et al. | 424/300 |
| 4,072,760 | 2/1978 | Hedegaard | 564/365 |
| 4,317,930 | 3/1982 | Hirose et al. | 564/363 |
| 4,379,166 | 4/1983 | Neustadt et al. | 564/363 |
| 4,730,008 | 3/1988 | Skidmore et al. | 546/232 |

FOREIGN PATENT DOCUMENTS 1214012 11/1970 United Kingdom .
1367668 9/1974 United Kingdom .
2140800A 12/1984 United Kingdom .

Primary Examiner—Richard L. Raymond
Assistant Examiner—Raymond Covington

[57] ABSTRACT

The present invention provides compounds of general formula (I)

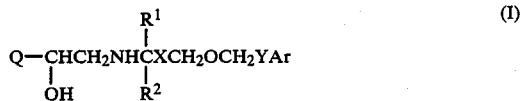

wherein
Ar represents an unsubstituted or substituted phenyl gorup;
$R^1$ and $R^2$ each represents a hydrogen atom or a $C_{1-3}$ alkyl group;
X represents a bond or a $C_{1-7}$ alkylene, $C_{2-7}$ alkenylene or $C_{2-7}$ alkynylene chain;
Y represents a bond or a $C_{1-6}$ alkylene, $C_{2-6}$ alkenylene or $C_{2-6}$ alkynylene chain;
Q represents a substituted phenyl or pyridyl ring;
and physiologically acceptable salts and solvates thereof useful as stimulants of 2-adrenoreceptors and particularly in the treatment of diseases associated with reversible airways obstruction such as asthma and chronic bronchitis.

9 Claims, No Drawings

ETHANOLAMINE DERIVATIVES

This is a continuation of co-pending application Ser. No. 919,123 filed on Oct. 15, 1986.

This invention relates to ethanolamine derivatives having a stimulant action at $\beta_2$-adrenoreceptors, to processes for their preparation, to pharmaceutical compositions containing them and to their use in medicine.

Ethanolamine derivatives of the general structure

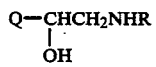

in which Q represents grouping of the type described hereinafter, and R represents inter alia an alkyl, aralkyl or aryloxyalkyl group have previously been described as bronchodilators having stimulant activity at $\beta$-adrenoreceptors. We have now found a novel group of ethanolamine derivatives which differ in structure from those described previously, and have a desirable and potentially useful profile of activity.

Thus, the present invention provides compounds of the general formula (I)

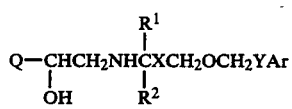

wherein Ar represents a phenyl group optionally substituted by one or more substituents selected from halogen atoms, or the groups $C_{1-6}$alkyl, nitro, $-(CH_2)_qR$, [where R is hydroxy, $C_{1-6}$ alkoxy, $-NR^3R^4$ (where $R^3$ and $R^4$ each represents a hydrogen atom, or a $C_{1-4}$alkyl group, or $-NR^3R^4$ forms a saturated heterocyclic amino group which has 5-7 ring members and optionally contains in the ring one or more atoms selected from $-O-$ or $-S-$ or a group $-NH-$ or $-N(CH_3)-$), $-NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or $-NR^3R^4$ group), $-NR^5SO_2R^7$ (where $R^7$ represents a $C_{1-4}$ alkyl, phenyl or $-NR^3R^4$ group), $-COR^8$ (where $R^8$ represents hydroxy, $C_{1-4}$ alkoxy or $-NR^3R^4$), $-SR^9$ (where $R^9$ is a hydrogen atom, or a $C_{1-4}$ alkyl or phenyl group), $-SOR^9$, $-SO_2R^9$, or $-CN$, and q represents an integer from 0 to 3], or $-O(CH_2)_tR^{10}$ [where $R^{10}$ represents a hydroxy or $C_{1-4}$ alkoxy group, and t is an integer 2 or 3], or Ar is a phenyl group substituted by an alkylenedioxy group of formula $-O(CH_2)_pO-$, where p represents an integer 1 or 2;

$R^1$ and $R^2$ each represents a hydrogen atom or a $C_{1-3}$ alkyl group with the proviso that the sum total of carbon atoms in $R^1$ and $R^2$ is not more than 4;

X represents a bond or a $C_{1-7}$ alkylene, $C_{2-7}$ alkenylene or $C_{2-7}$ alkynylene chain and Y represents a bond or a $C_{1-6}$ alkylene, $C_{2-6}$ alkenylene or $C_{2-6}$ alkynylene chain with the proviso that the sum total of carbon atoms in X and Y is 2-10;

Q represents the group

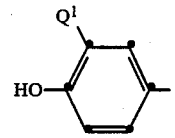

[where $Q^1$ represents the group $-CH_2R^{23}$ (where $R^{23}$ represents $C_{1-3}$ alkoxy, methanesulphonyl or cyano), or the group $-CH_2NHR^{11}$ (where $R^{11}$ represents $R^{12}CO-$, $R^{12}NHCO-$, $R^{12}R^{13}NSO_2-$ or $R^{14}SO_2-$, where $R^{12}$ and $R^{13}$ each represent a hydrogen atom or a $C_{1-3}$ alkyl group, and $R^{14}$ represents a $C_{1-3}$ alkyl group), or the group $-NR^{15}R^{16}$ (where $R^{15}$ represents a hydrogen atom or a $C_{1-4}$alkyl group, and $R^{16}$ represents a hydrogen atom or a $C_{1-4}$alkyl group or, when $R^{15}$ is a hydrogen atom, $R^{16}$ also represents a $C_{1-4}$alkoxycarbonyl group)], or Q represents the group

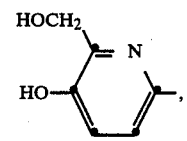

or Q represents a phenyl group substituted by hydroxy group and optionally also by a halogen atom; and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached.

The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In one aspect the invention provides compounds of the formula (Ia)

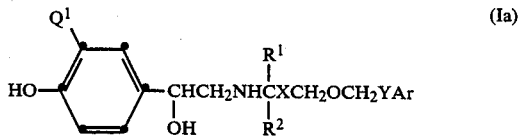

wherein $Q^1$ represents the group $-CH_2R^{23}$, and $R^{23}$, $R^1$, $R^2$, X, Y and Ar are as defined for formula (I).

In another aspect the invention provides compounds of formula (Ia) in which $Q^1$ represents the group —CH₂NHR¹¹, and R¹¹, R¹, R², X, Y and Ar are as defined for formula (I).

In a further aspect the invention provides compounds of formula (Ia) in which Q¹ represents the group —NR¹⁵R¹⁶, and R¹⁵, R¹⁶, R¹, R², X, Y and Ar are as defined for formula (I).

In yet another aspect the invention provides compounds of formula (Ib)

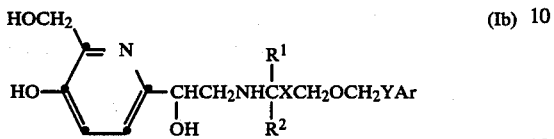
(Ib)

wherein R¹, R², X, Y and Ar are as defined for formula (I).

In a still further aspect the invention provides compounds of formula (I) in which Q represents a phenyl group substituted by a hydroxy group and optionally also by a halogen atom, and R¹, R², X, Y and Ar are as defined for formula (I).

In the general formula (I), the chain X may for example contain 1 to 7 carbon atoms and may be for example —CH₂—, —(CH₂)₂—, —(CH₂)₃—, —(CH₂)₄—, —(CH₂)₅—, —CH₂C≡C—, —(CH₂)₂CH=CH—, —(CH₂)₂C≡C—, —CH=CHCH₂—, —CH=CH(CH₂)₂— or —CH₂C≡CCH₂—. The chain Y may be for example a bond, —CH₂—, —(CH₂)₂—, —(CH₂)₃—, —(CH₂)₄—, —(CH₂)₅—, —(CH₂)₆—, —CH=CH—, —C≡C—, —CH₂CH=CH— or —CH₂C≡C—.

In general, the total number of carbon atoms in the chains X and Y is preferably 4 to 10 inclusive and may be for example 5, 6, 7 or 8. Compounds wherein the sum total of carbon atoms in the chains X and Y is 5, 6 or 7 are particularly preferred.

One preferred group of compounds of formula (I) is that in which X is C₁₋₇ alkylene, Y is C₁₋₆ alkylene and Q, Ar, R¹ and R² are as defined for formula (I). Particular compounds of this type are those in which X is —(CH₂)₃— or —(CH₂)₄—, and Y is —CH₂—, —(CH₂)₂— or —(CH₂)₃—.

In the compounds of formula (I) R¹ and R² may each be for example methyl, ethyl, propyl or isopropyl groups except that if one of R¹ and R² is a propyl or isopropyl group, the other is a hydrogen atom or a methyl group. Thus for example R¹ may be hydrogen atom or a methyl, ethyl or propyl group. R² may be for example a hydrogen atom or a methyl group. R¹ and R² are each preferably a hydrogen atom or a methyl group.

A preferred group of compounds is that wherein R¹ and R² are both hydrogen atoms, or R¹ is a hydrogen atom and R² is a C₁₋₃ alkyl group, particularly a methyl group.

When Q¹ represents the group —CH₂R²³, R²³ preferably represents a C₁₋₃ alkoxy group, more preferably methoxy.

When Q¹ represents the group —CH₂NHR¹¹ and R¹¹ represents R¹²CO—, R¹²NHCO—, R¹²R¹³NSO₂— or R¹⁴SO₂—, R¹² and R¹³ may each be for example a hydrogen atom or a methyl, ethyl, propyl or isopropyl group, and R¹⁴ may be a methyl, ethyl, propyl, isopropyl or butyl group. Examples of the group R¹¹ are HCO—, CH₃CO—, NH₂CO—, NH₂SO₂— and CH₃SO₂—.

When Q¹ represents the group —NR¹⁵R¹⁶, R¹⁵ and R¹⁶ may each be for example a hydrogen atom or a methyl, ethyl, n-propyl, isopropyl, n-butyl, i-butyl, sec-butyl or t-butyl group. Alternatively, when R¹⁵ is a hydrogen atom, R¹⁶ may be for example a methoxycarbonyl or ethoxycarbonyl group. In one preferred group of compounds R¹⁵ is a hydrogen atom and R¹⁶ is a methyl group.

When Q represents a phenyl group substituted by a hydroxy group and optionally also a halogen atom, the halogen atom may be a chlorine or, more preferably, a fluorine atom. Specific examples of this meaning for the group Q are

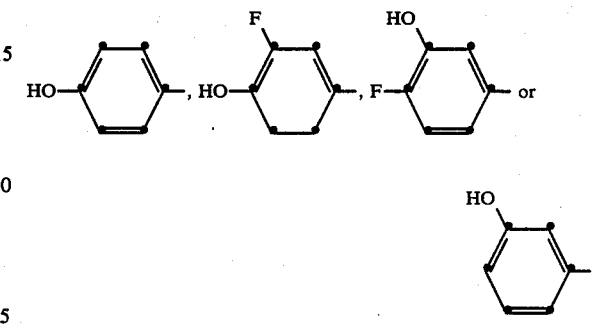

When —NR³R⁴ in compounds of formula (I) represents a saturated heterocyclic amino group, this may have 5, 6 or 7 ring members and optionally contain in the ring a heteroatom selected from —O— or —S—, or a group —NH— or —N(CH₃)—. Examples of such —NR³R⁴ groups are pyrrolidino, piperidino, hexamethylenimino, piperazino, N-methylpiperazino, morpholino, homomorpholino or thiamorpholino.

Ar may be for example a phenyl group. Examples of the substituents which may be present on the phenyl group represented by Ar include chlorine, bromine, iodine, fluorine, methyl, ethyl, methoxy, ethoxy, —(CH₂)qR [where R is hydroxy, methoxy, amino, methylamino, ethylamino, dimethylamino, diethylamino, morpholino, pyrrolidino, piperidino, piperazino, N-methylpiperazino, NHCOR⁶ (where R⁶ is hydrogen or C₁₋₄ alkyl e.g. methyl, ethyl, isopropyl or n-butyl, C₁₋₄ alkoxy e.g. methoxy, ethoxy, isopropoxy, or n-butoxy, phenyl, amino or N,N-dimethylamino), —N(CH₃)COCH₃, —NR⁵SO₂R⁷ (where R⁵ represents a hydrogen atom or a methyl group and R⁷ represents methyl, butyl, phenyl, amino or dimethylamino), —COOH, —COOCH₃, —CONH₂, —CON(CH₃)₂, —CON(CH₂CH₃)₂,

,

—SR⁹ (where R⁹ is methyl, ethyl or phenyl), —SOCH₃, —SO₂CH₃, or CN and q is zero, 1, 2 or 3], —NO₂, —O(CH₂)₂OH, —O(CH₂)₃OH, —O(CH₂)₂OCH₃, or —O(CH₂)₂OCH₂CH₃.

The phenyl group represented by Ar may optionally contain one, two or three substituents, which may be present at the 2-, 3-, 4-, 5- or 6-positions on the phenyl ring.

Particular examples of a trisubstituted phenyl group represented by Ar include phenyl substituted by an amino and two methyl groups (e.g. 3,5-dimethyl-4- aminophenyl), an amino group and two chlorine atoms (e.g. 3,5-dichloro-4-aminophenyl, or three methoxy groups (e.g. 3,4,5-trimethoxyphenyl). Particular examples of a disubstituted phenyl group represented by Ar include phenyl substituted by two hydroxyl groups (e.g. 3,5-dihydroxyphenyl), a hydroxyl and methoxy group (e.g. 3-methoxy-4-hydroxyphenyl,) or two methyl groups (e.g. 3,4-dimethylphenyl).

In one preferred group of compounds, Ar is phenyl or phenyl substituted by a halogen atom (e.g. fluorine), or by a group selected from $C_{1-4}$ alkyl (e.g. methyl), $C_{1-4}$ alkoxy (e.g. methoxy), a 5-7 membered heterocyclic amino group (e.g. pyrrolidine or piperidine), $-SR^9$ (where $R^9$ is $C_{1-4}$ alkyl e.g. methyl), $-CONR^3R^4$ (where $R^3$ and $R^4$ represent $C_{1-4}$ alkyl e.g. ethyl), $-NHSO_2R^7$ (where $R^7$ is $C_{1-4}$ alkyl e.g. butyl), or $-(CH_2)_qNHCOR^6$ (where q is zero or 1, and $R^6$ is $C_{1-4}$ alkyl e.g. methyl or butyl), or Ar represents phenyl substituted by methoxy and hydroxy (e.g. 3-methoxy-4-hydroxy).

Preferred compounds according to the invention are
3-fluoro-4-hydroxy-α-[[[6-(2-phenylethoxy)hexyl]amino]methyl]benzenemethanol;
3-fluoro-4-hydroxy-α-[[[6-(4-phenylbutoxy)hexyl]amino]methyl]benzenemethanol;
3-fluoro-4-hydroxy-α-[[[6-[3-[4-(methylthio)phenyl]propoxy]hexyl]amino]methyl]benzenemethanol;
N,N-diethyl-4-[4-[[6-[[2-(3-fluoro-4-hydroxyphenyl)-2-hydroxyethyl]amino]hexyl]oxy]butyl]benzamide;
N,N-diethyl-4-[4-[[6-[2-hydroxy-2-(3-hydroxyphenyl)ethyl]amino]hexyl]oxy]butyl]benzamide;
4-hydroxy-3-(methoxymethyl)-α-[[[6-[2-(4-methoxyphenyl)ethoxy]hexyl]amino]methyl]benzenemethanol;
4-hydroxy-3-(methoxymethyl)-α-[[[6-[3-phenylpropoxy]hexyl]amino]methyl]benzenemethanol;
[4-hydroxy-3-(methoxymethyl)]-α-[[[1-methyl-5-[3-[4-(1-pyrrolidinyl)phenyl]propoxy]pentyl]amino]methyl]benzenemethanol;
3-hydroxy-α$^6$-[[[1-methyl-6-(2-phenylethoxy)hexyl]amino]methyl]-2,6-pyridinedimethanol;
α$^6$-[[[6-[4-(4-fluorophenyl)butoxy]hexyl]amino]methyl]-3-hydroxy-2,6-pyridinedimethanol; and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, sulphamates, ascorbates, salicylates, acetates, fumarates, succinates, lactates, glutarates, gluconates, tricarballylates, hydroxy-naphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium or magnesium) salts.

The compounds according to the invention have a selective stimulant action at $β_2$-adrenoreceptors, which furthermore is of a particularly advantageous profile. The stimulant action was demonstrated in the isolated trachea of the guinea-pig, where compounds were shown to cause relaxation of PGF2α-induced contractions. Compounds according to the invention have shown a advantageous duration of action in this test.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammatory and allergic skin diseases, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a conventional manner in forms suitable for administration by inhalation or insufflation, or for oral, buccal, parenteral, topical (including nasal) or rectal administration. Administration by inhalation or insufflation is preferred. The pharmaceutical compositions may be prepared by conventional means, using physiologically acceptable excipients.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes, as described in the following. In the following description of processes for preparing compounds of formula (I) and intermediates which may be used in the preparation thereof, Q, X, Y, Ar, $R^1$ and $R^2$ are as defined for general formula (I) unless otherwise specified, or Ar may contain precursor substituent(s) convertible to the required substituent(s) by conventional means. It will be appreciated that certain of the reactants described below are capable of affecting other groups in the starting material which are desired in the end product; this applies especially in the reduction processes described, particularly where a hydride reducing agent is used in the preparation of compounds containing an acid, ester or amide function, or where hydrogen and a metal catalyst are used in the preparation of compounds containing an ethylene or acetylene linkage. Care must therefore be taken in accordance with conventional practice, either to use reagents which will not affect such groups, or to perform the reaction as part of a sequence which avoids their use when such groups are present in the starting material. In the preparation of both intermediates and end-products the final step in the reaction may be the removal of a protecting group. Suitable protecting groups and their removal are described in general process (3) below.

According to one general process (1), a compound of general formula (I) may be obtained by reaction of a compound of general formula (II):

$$QZ \quad (II)$$

(wherein any hydroxyl and/or amino substituents in Q may optionally be protected, and Z represents a group

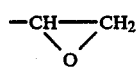

or

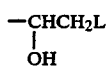

where L represents a leaving group, for example a halogen atom such as chlorine, bromine or iodine, or a hydrocarbylsulphonyloxy group such as methanesulphonyloxy or p-toluenesulphonyloxy) with an amine of general formula (III)

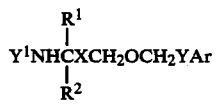

(wherein $Y^1$ is a hydrogen atom or a group convertible thereto by catalytic hydrogenation) followed by removal of any protecting groups where present, as described hereinafter.

Suitable $Y^1$ groups convertible into a hydrogen atom include arylmethyl groups such as benzyl, benzhydryl, or α-methylbenzyl.

The reaction may be effected in the presence of a suitable solvent for example an alcohol, such as ethanol, a halogenated hydrocarbon e.g. chloroform, a substituted amide e.g. dimethylformamide or an ether such as tetrahydrofuran or dioxan at a temperature from ambient to the reflux, optionally in the presence of a base such as an organic amine e.g. diisopropylethylamine or an inorganic base such as sodium carbonate.

In another general process (2), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (IV)

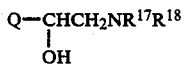

(wherein $R^{17}$ is a hydrogen atom or a protecting group, $R^{18}$ is a hydrogen atom and any hydroxyl and/or amino substituents in Q may optionally be protected) followed by removal of any protecting group where present.

The alkylation reaction (a) may be effected using an alkylating agent of general formula (V):

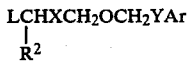

(wherein L is as previously defined).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (IV) as previously defined except that $R^{18}$ is a hydrogen atom or a group convertible thereto under the reaction conditions, with a compound of general formula (VI):

in the presence of a reducing agent, followed when necessary by removal of any protecting groups.

Examples of suitable $R^{18}$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres.

Alternatively when one or both of $R^{17}$ and $R^{18}$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (IV) where $R^{17}$ and $R^{18}$ are each hydrogen atoms is used, the intermediate imine of formula (VII) may be formed:

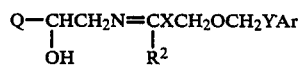

Reduction of the imine using the conditions described above, followed, where necessary, by removal of any protecting groups, gives a compound of general formula (I).

Where it is desired to use a protected intermediate of general formula (IV) it is particularly convenient to use hydrogen and a metal catalyst as described above with protecting group $R^{17}$ which is capable of being converted to a hydrogen atom under these reducing conditions, thus avoiding the need for a separate deprotection step. Suitable protecting groups of this type include arylmethyl groups such as benzyl, benzhydryl and α-methylbenzyl.

In another general process (3), a compound of general formula (I) may be obtained by deprotection of a protected intermediate of general formula (VIII):

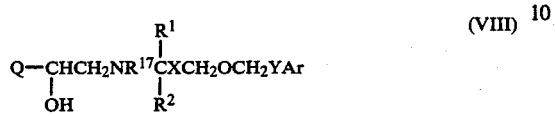
(VIII)

(wherein Q and $R^{17}$ are as defined in formula (IV) and either $R^{17}$ is a protecting group and/or at least one of the amino and/or hydroxyl substituents in Q is protected).

The protecting groups may be any conventional protecting groups, for example as described in "Protective Groups in Organic Chemistry", Ed. J. F. W. McOmie (Plenum Press, 1973). Examples of suitable amino protecting groups within the group Q and represented by $R^{17}$ are arylmethyl groups such as benzyl, α-methylbenzyl, diphenylmethyl or triphenylmethyl and acyl groups such as tricholoroacetyl or trifluoroacetyl. Examples of suitable hydroxyl protecting groups within the group Q are tetrahydropyranyl or arylmethyl groups such as benzyl, diphenylmethyl or triphenylmethyl. The deprotection to yield a compound of general formula (I) may be effected using conventional techniques. Thus for example, an arylmethyl group may be cleaved by hydrogenolysis in the presence of a metal catalyst (e.g. palladium on charcoal). Tetrahydropyranyl groups may be cleaved by hydrolysis under acidic conditions. Acyl groups may be cleaved by hydrolysis, for example with a base such as sodium hydroxide, or a group such as trichloroacetyl may be removed by reduction with, for example, zinc and acetic acid.

In a particular embodiment of the deprotection process a compound of formula (I) in which Q represents the group

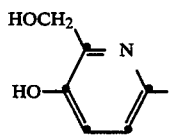

may be obtained by deprotecting a compound of formula (IX)

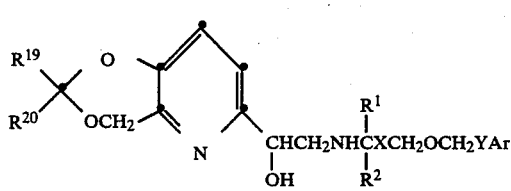
(IX)

(wherein $R^{19}$ and $R^{20}$, which may be the same or different, each represents a hydrogen atom or an alkyl or aryl group). The deprotection may be effected by treatment with a dilute acid, for example hydrochloric acid, in a solvent such as water or an alcohol such as ethanol at normal or elevated temperature.

In another general process (4), a compound of general formula (I) may be prepared by reduction. Thus, for example, a compound of general formula (I) may be prepared by reducing an intermediate of general formula (X):

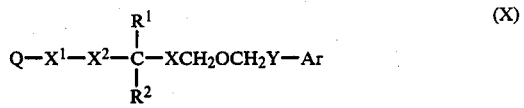
(X)

(wherein any hydroxyl and/or amino substituents in Q may optionally be protected, and at least one of $X^1$ and $X^2$ represents a reducible group and/or Q, X, Y and/or Ar contains a reducible group, and the other(s) take the appropriate meaning as follows, which is $X^1$ is —CH(OH)—, $X^2$ is —$CH_2NR^{17}$ (where $R^{17}$ is as defined in formula IV), X is a bond or $C_{1-7}$ alkylene, Y is a bond or $C_{1-6}$ alkylene, and Q and Ar are defined in formula (I). Where necessary the reduction may be followed by removal of any protecting groups.

Suitable reducible groups include those wherein $X^1$ is a group >C=O, $X^2$ is a group —$CH_2NY^1$— (wherein $Y^1$ represents a group convertible to hydrogen by catalytic hydrogenation, for example an arylmethyl group such as benzyl, benzhydryl or α-methylbenzyl). In one convenient aspect of the reduction process, the hydrogen atom of any hydroxyl substituent in the group Q may represent a group convertible to hydrogen under the reducing conditions employed and may be for example an arylmethyl group such as benzyl, benzhydryl or α-methylbenzyl.

The reduction may be effected using reducing agents conveniently employed for the reduction of ketones, protected amines, alkenes and alkynes.

Thus, for example, when $X^1$ in general formula (X) represents a >C=O group this may be reduced to a —CH(OH)— group using hydrogen in the presence of a metal catalyst as previously described for process (2) part (b). Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (X) represents a —$CH_2NY^1$— group this may be reduced to a —$CH_2NH$— group, and/or when X and/or Y is an alkenylene or alkynylene chain this may be reduced to an alkylene chain. These reductions may be effected using hydrogen in the presence of a metal catalyst as previously described for process (2) part (b).

In a further example of reduction process (4) a compound of formula (I) in which Q represents the group

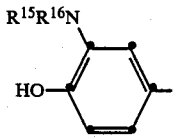

(wherein R$^{15}$ is as defined in formula I, and R$^{16}$ represents an alkyl group) may be prepared by reducing an intermediate of formula (XI)

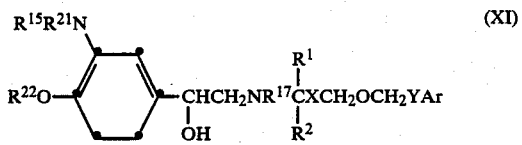   (XI)

(wherein R$^{17}$ and R$^{22}$ each represent a hydrogen atom or a protecting group, and R$^{21}$ represents an alkoxycarbonyl, aryloxycarbonyl, C$_{2-4}$ alkanoyl or formyl group) followed where necessary by removal of any protecting group. The reduction may be effected using a reducing agent such as a metal hydride e.g. lithium aluminium hydride in a solvent such as an ether e.g. tetrahydrofuran.

In the general processes described above, the compound of formula (I) obtained may be in the form of a salt, conveniently in the form of a physiologically acceptable salt. Where desired, such salts may be converted to the corresponding free acids using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

Intermediates of formula (II) in which Z represents a group

—CHCH$_2$Hal
 |
 OH may be prepared from a haloketone of formula (XII): 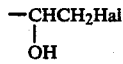

Q—COCH$_2$Hal   (XII)

(wherein Q is as defined in formula (I) with any amino and/or hydroxyl substituents optionally protected, and Hal represents a halogen atom) by reduction using for example a metal hydride such as sodium borohydride in a solvent such as ethanol.

The halogen atom may be displaced to yield other compounds of general formula (II) in which Z is a group —CHCH$_2$L where L is a leaving group other than a halogen OH atom.

Compounds of formula (II) wherein Z represents

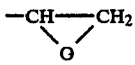

may be prepared from the corresponding compound in which Z is

by treatment with base, for example an amine, which may be for example a compound of general formula (III), or an inorganic base such as sodium hydroxide in a solvent such as ethanol.

The amines of formula (IV), haloketones of formula (XII) and the intermediates of formulae (III), (V) and (VI) are either known compounds or may be prepared by methods analogous to those used for the preparation of known compounds. Suitable methods for preparing intermediates of formulae (III), (V) and (VI) are described in U.K. patent specifications Nos. 2,140,800A, 2,159,151A, 2,162,842A and 2,165,542, European published Patent Appliations Nos. 162,576 and 178,919, and in the exemplification included hereinafter.

Intermediate compounds of general formula (X) for use in general process (4) may be prepared by a number of processes.

Thus for example intermediates of general formula (X) in which X$^1$ is a group >C=O may be prepared from a haloketone of formula (XII) by reaction with an amine of general formula (III). The reaction may be effected in a cold or hot solvent, for example tetrahydrofuran, tert-butyl methyl ether, dioxan, chloroform, dimethylformamide, acetonitrile or a ketone such as butanone or methylisobutylketone, or an ester, for example ethyl acetate preferably in the presence of a base such as diisopropylethylamine, sodium carbonate or other acid scavenger such as propylene oxide.

Intermediates of general formula (X) in which X$^1$ is a group >C=O may be reduced to the corresponding intermediate in which X$^1$ is a group —CH(OH)— using for example a metal hydride such as sodium borohydride in a solvent e.g. ethanol.

The following examples illustrate the invention. Temperatures are in °C. Drying refers to drying using magnesium sulphate or sodium sulphate except where otherwise stated. Thin layer chromatography (t.l.c.) was carried out over SiO$_2$, and flash column chromatography (FCC) on silica (Merck 9385), using, unless otherwise stated, one of the following solvent systems: System A, ethyl acetate:methanol:triethylamine; System B, toluene: ethanol:triethylamine; System C, toluene:ethanol:0.88 ammonia; System D, ethyl aetate:-methanol:0.88 ammonia; System E, cyclohexane:ethyl acetate:triethylamine. The following abbreviations are used: THF-tetrahydrofuran, DMF-dimethylformamide, TAB-tetra-n-butylammonium sulphate, DEA-diisopropylethylamine, BTPC - bis(triphenylphosphine) palladium(II)chloride, Pt-C platinum on carbon, PdO-C palladium oxide on carbon, Pd-C palladium on charcoal, PtO-C platinum oxide on carbon, EA-ethyl acetate, ER-diethyl ether, CX-cyclohexane, H-hexane, PE-light petroleum (b.p. 40°–60°).

Intermediate 1 is α-(Aminoethyl)-2-phenyl-4H-1,3-dioxino[5,4-b]pyridine-6-methanol.

Intermediate 2

α-[[[1-Methyl-6-(2-phenylethoxy)hexyl]amino]methyl]-2-phenyl-4H-1,3-dioxino[5,4-b]pyridine-6-methanol Intermediate 1 (830 mg) and 7-[2-(phenylethoxy)]-2-heptane (714 mg) were hydrogenated in ethanol (25 ml) over 5% Pt-C (90 mg) and 10% PdO-C (50% paste with water, 100 mg). The catalyst was removed by filtration through hyflo and the ethanol was evaporated. The residual oil was purified by FCC eluting with System A (99:0:1→90:10:1) to give the title compound as a white solid (690 mg) m.p. 61°–67°, t.l.c. (System A 80:20:1) Rf 0.33.

Intermediate 3

2-Phenyl-α-[[[6-(4-phenylbutoxy)hexyl]amino]methyl]-4H-1,3-dioxino[5,4-b]pyridine-6-methanol

[4-(6-Bromohexyl)butyl]benzene (2.0 g) was added to a stirred solution of Intermediate 1 (3.0 g) and DEA (1.8 g) in DMF (50 ml) at 75° under nitrogen. The reaction mixture was stirred at 75° for 3 h, the solvent was evaporated and the residue was purified by FCC eluting with System A (99:0:1→90:10:1) to give the title compound as a pale brown solid (1.9 g) m.p. 67°–73°, t.l.c. (System B 95:5:1) Rf 0.1.

Intermediate 4

6-[[3-[4-(1-Piperidinyl)phenyl]-2-propynyl]oxy]hexanol

A mixture of 1-(4-iodophenyl)piperidine (1.5 g), 6-[(2-propynyl)oxy]-1-hexanol (820 mg), BTPC (35 mg) and copper (I) iodide (20 mg) in diethylamine (30 ml) under nitrogen, was stired at room temperature overnight. The solvent was evaporated and the residue was partitioned between EA (50 ml) and 8% aqueous sodium bicarbonate (50 ml). The organic layer was washed with water and brine, dried and concentrated to a dark oil which was purified by FCC eluting with ER to give the title compound as an orange oil (1.2 g), t.l.c. (ER) Rf 0.70.

Intermediate 5

6-[3-[4-(1-Piperidinyl)phenyl]propoxy]hexanol

Intermediate 4 (1.2 g) was hydrogenated in ethanol (15 ml) over pre-reduced 10% PdO-C (200 mg). The catalyst was removed by filtration through hyflo and the ethanol was evaporated to give the title compound as an orange oil (1.15 g), t.l.c. (ER) Rf 0.71.

Intermediate 6

1-[4-[3-[(6-Bromohexyl)oxy]propyl]phenyl]piperidine

A solution of triphenylphosphine (950 mg) in dichloromethane (5 ml) was added dropwise to an ice-bath cooled solution of Intermediate 5 (1.1 g) and carbon tetrabromide (1.2 g) in dichloromethane (10 ml). The solution was stirred at 0° for 1 h, evaporated onto silica, and purified by FCC eluting with hexane/ER (9:1) to give the title compound as a colourless oil (1.0 g), t.l.c. (H/ER 9:1) Rf 0.32.

Intermediate 7

2-Phenyl-α-[[[6-[3-[4-(1-piperidinyl)phenyl]propoxy]hexyl]amino]methyl]-4H-1,3-dioxino[5,4-b]pyridine-6-methanol A solution of Intermediate 6 (950 mg) in dry DMF (2 ml) was added to a stirred solution of Intermediate 1 (1.36 g) and DEA (650 mg) in dry DMF (30 ml) at 90° under nitrogen. After 3 h, the solvent was evaporated and the product was purified by FCC eluting with System B (95:5:1) to give the title compound as a white solid (680 mg) m.p. 75°–76°.

Intermediate 8

N-[4-[4-[[6-[[2-Hydroxy-2-(2-phenyl-4H-1,3-dioxino[5,4-b]pyridin-6-yl)ethyl]amino]hexyl]oxy]butyl]phenyl]butanesulphonamide N-[4-[4-[(6-Bromohexyl)oxy]butyl]phenyl]butanesulphonamide (1.35 g) was added to a solution of Intermediate 1 (1.2 g) and DEA (1.13 g) in DMF (35 ml) at 80°. The solution was stirred at 80° for 3 h, the solvent we evaporated and the residue was purified by FCC eluting with System B (95:5:1) to give the title compound as a dark foam (520 mg), which was used without further purification.

Intermediate 9

2-Phenyl-α-[[[3-[(6-phenylhexyl)oxy]propyl]amino]methyl]-4H-1,3-dioxino[5,4-b]pyridine-6-methanol A mixture of Intermediate 1 (1.5 g), [6-(3-bromopropoxy)hexyl]benzene (1.1 g) and DEA (0.95 g) in DMF (30 ml) was stirred at 100° under nitrogen for 1 h. The solution was evaporated in vacuo and purified by FCC eluting with System B (95:5:1) to give an orange oil. This oil crystallised on standing to give the title compound as a cream solid (0.70 g) m.p. 64°–68°, t.l.c. (System B 95:5:1) Rf 0.14.

Intermediate 10

4-(4-Fluorophenyl)-3butyn-1-ol

Copper (I) iodide was added to a stirred solution of 1-fluoro-4-iodobenzene (11.09 g), 3-butyn-1-ol (3.5 g), and BTPC (100 g) in diethylamine (70 ml) and the mixture stirred under nitrogen for 16 h. The mixture was evaporated in vacuo and purified by FCC on eluting with H - EA (2:1) gave the title compound as a yellow solid (2.8 g). T.l.c. (H - EA 2:1) RF 0.20.

Intermediate 11

1-[[4-[(6-Bromohexyl)oxy]]-1-butynyl]-4-fluorobenzene

A mixture of Intermediate 10 (2.5 gm), 1,6-dibromohexane (11.4 g) and TAB (0.5 g) in 40% sodium hydroxide (20 ml) was stirred at room temperature for 18 h, diluted with water (150 ml) and extracted with ER (2×150 ml). The organic layer was washed with brine (100 ml), dried (MgSO4) and evaporated in vacuo to give an oil. Purification by FCC eluting with CX-EA (10:0→9:1) gave the title compound as a colourless oil (4.62 g). T.l.c. (CX-EA 9:1) Rf 0.46.

Intermediate 12

α-[[[6-[[4-(4-Fluorophenyl)-3-butynyl]oxy]hexyl]amino]methyl-2-phenyl-4H-1,3-dioxino[5,4-b]pyridine-6-methanol A mixture of Intermediate 1 (1.5 g), Intermediate 11 (1.16 g) and DEA (0.9 g) in DMF (30 ml) was stirred at 100° under nitrogen for 1.5 h. The solvent was evaporated and the residual oil purified by FCC eluting with System B (95:5:1) affording a colourless oil. Trituration with ER gave the title compound as a white solid (1.02 g) m.p. 83°–85°, t.l.c. (System B 95:5:1) Rf 0.19.

Intermediate 13

α-[[[6-[4-(4-Methylphenyl)butoxy]hexyl]amino]methyl]-2-phenyl-4H-1,3-dioxino[5,4-b]pyridine-6-methanol A solution of Intermediate 1 (1.5 g), 1-[4-[(6-bromohexyl)oxy]butyl]-4-methylbenzene (1.20 g) and DEA (1.42 g) in DMF (30 ml) was stirred at 100° under nitrogen for 1 h. The reaction mixture was concentrated to give a solid which was purified by FCC eluting with System B (95:5:1) to give the title compound as a cream solid (1.18 g) m.p. 74°.

Intermediate 14

1-[3-[(6-Bromohexyl)oxy]propyl]-4-(methylthio)benzene

A mixture of 4-(methylthio)benzenepropanol (5.0 g) 1,6-dibromohexane (17.0 g) aqueous sodium hydroxide (50% w/v, 20 ml) and TAB (0.4 g) was stirred at room temperature for 20 h, diluted with water (30 ml), and extracted with ER (2×100 ml). The dried extract was evaporated and the residue was purified by FCC eluting with CX followed by CX-ER ether (19:1) to give the title compound as a colourless oil (7.0 g). T.l.c. (CX-ER 9:1) Rf 0.5.

Intermediate 15

α-[[[6-[3-[4-(methylthio)phenyl]propoxy]hexyl]amino]methyl]-2-phenyl-4H-1,3-dioxino[5,4-b]pyridine-6-methanol A solution of Intermediate 1 (1.5 g), Intermediate 14 (1.27 g) and DEA (1.42 g) in DMF (30 ml) was stirred at 100° under nitrogen for 1 h. The reaction mixture was concentrated to a solid which was purified by FCC eluting with System B (95:5:1) to give the title compound as a white solid (0.88 g) m.p. 70°.

Intermediate 16

(E)-4-[3-Methoxy-4-(phenylmethoxy)phenyl]-3-buten-1-ol n-Butyllithium (1.55M in hexane, 194 ml) was added dropwise to a stirred suspension of (3-hydroxypropyl)-triphenylphosphonium bromide (60.3 g) in dry THF (375 ml) cooled to 0° under nitrogen. The resulting blood-red solution was stirred at 0° for 15 min and then a solution of 3-methoxy-4-(phenylmethoxy) benzaldehyde (36.3 g) in dry THF (50 ml) added dropwise over 15 min. The mixture was stirred at 0° for 30 min, allowed to warm up to room temperature, stirred for a further 2 h and then the reaction quenched by the addition of 2N hydrochloric acid (100 ml). The THF was removed in vacuo at 40°, the aqueous residue extracted with EA (350 ml) and the organic layer washed with 2N HCl (200 ml). The aqueous phase was extracted with further EA (150 ml), the organic layers combined, washed with 8% sodium bicarbonate solution (200 ml) and dried (MgSO$_4$). Concentration afforded the crude product which was purified by FCC eluting with EA-CX (1:2) yielding the title compound as a cream powder (14.5 g) m.p. 57°–61° T.l.c. (ER-CX - 1:1) Rf 0.15.

Intermediate 17

(E)-1-[4-[(6-Bromohexyl)oxy]-1-butenyl]-3-methoxy-4-(phenylmethoxy)benzene

A mixture of Intermediate 16 (12.0 g) 1,6-dibromohexane (41.2 g), 50% w/v aqueous sodium hydroxide solution (68 ml) and TAB (1.44 g) was vigorously stirred at room temperature for 18 h. Water (250 ml) was added, the mixture extracted with ER (2×200 ml) and the organic layer washed with water (150 ml) and dried. The ER was removed in vacuo at 35°, and the majority of the excess dibromide removed by distillation under high vacuum (b.p. ~60°/1 mmHg) to afford the crude product as a viscous yellow oil. This was purified by FCC eluting with ER-CX (1:5) to give the title compound as a colourless oil (11.2 g). T.l.c. (ER-CX - 1.3) Rf 0.43.

Intermediate 18

(E)-N-[6-[[4-[3-Methoxy-4-(phenylmethoxy)phenyl]-3-butenyl]oxy]hexyl]benzenemethanamine Intermediate 17 (2.23 g) was added dropwise to benzylamine (10 ml) stirred at 120° under nitrogen and the solution heated at 120° for a further 2 h. The mixture was cooled, poured into 2N hydrochloric acid (100 ml) and extracted with dichloromethane (2×75 ml). The organic layer was washed with 2N hydrochloric acid, 8% sodium bicarbonate solution (75 ml), dried and concentrated in vacuo at 40° to afford the title compound as a pale yellow oil (2.32 g), t.l.c. (System C - 39:10:1) Rf 0.41.

Intermediate 19

(E)-α-[[[6-[[4-[3-Methoxy-4-(phenylmethoxy)phenyl]-3-butenyl]oxy]hexyl]amino]methyl]-2-phenyl-4H,1,3-dioxino[5,4-b]pyridine-6-methanol Intermediate 18 (2.19 g) in DMF (5 ml) was added to Intermediate 1 (2.0) and DEA (1.9 g) in DMF (25 ml) at 100° under nitrogen. The reaction was stirred for 2 h at 100° and after 16 h at room temperature the solution was concentrated. The resultant residue was purified by FCC eluting with System B (95:5:1) to give the title compound as an off-white solid (1.79 g) m.p. 108°–110°.

Intermediate 20

N-[[4-[4-[[6-[[2-Hydroxy-2-(2-phenyl-4H-1,3-dioxino[5,4-b]pyridin-6-yl]ethyl](phenylmethyl)amino]hexyl]oxy]-1-butynyl]phenyl]methyl]pentanamide A solution of 6-oxiranyl-2-phenyl-4H-1,3-dioxino[5,4-b]pyridine (0.712 g) and N-[[4-[4-[[6-[(phenylmethyl)amino]hexyl]oxy]-1-butynyl]phenyl]methyl]pentanamide (1.25 g) in methanol (10 ml) was refluxed for 11 h. The methanol was evaporated to leave an oil which was purified by FCC eluting with ER to give the title compound as a yellow oil (1.02 g), t.l.c. ER:triethylamine (100:1) Rf 0.2

Intermediate 21

N-[[4-[4-[[6-[[2-Hydroxy-2-(3-hydroxy-2-(hydroxymethyl)pyridine-6-yl]ethyl](phenylmethyl)amino]hexyl]oxy]-1-butynyl]phenyl]methyl]pentanamide A solution of Intermediate 20 (0.51 g) and 2N hydrochloric acid (3 ml) in methanol (10 ml) was stirred for 16 h. The reaction mixture was concentrated and the residue partitioned between EA (50 ml) and 8% aqueous sodium bicarbonate (2×50 ml). The organic layer was washed with brine (30 ml), dried and concentrated to give an oil (0.44 g) which was purified by FCC eluting with System B (80:20:1) to give the title compound as a yellow oil (0.34 g), t.l.c. (System C 39:1:1)) Rf 0.25.

Intermediate 22

α-[[[6-[4-(4-Methoxyphenyl]butoxy]hexyl]amino]methyl-2-phenyl-4H-1,3-dioxino[5,4-b]pyridine-6-methanol 1-[4-[(6-Bromohexyl)oxy]butyl]-4-methoxybenzene (2.0 g) was added to a solution of Intermediate 1 (2.2 g) and DEA (1.3 g) in DMF (40 ml) at 100° under nitrogen. After 2 h the solvent was removed under vacuum and the residue was partitioned between 8% sodium bicarbonate (50 ml) and EA (50 ml). The organic layer was washed with brine, dried and concentrated to a red sludge which was purified by FCC eluting with System B (90:10:1) to give the title compound as a buff solid (1.75 g) m.p. 69°–72°, t.l.c. (System B 90:10:1) Rf 0.18.

Intermediate 23

5-[1-Hydroxy-2-[[[6-(4-phenylbutoxy)hexyl](phenylmethyl)amino]ethyl]-2-(phenylmethoxy)benzamide A mixture of 5-(bromoacetyl)-2-(phenylmethoxy)benzamide (9.0 g), N-[6-(4-phenylbutoxy)hexyl]benzenemethanamine (8.7 g), DEA (3.3 g) and THF (80 ml) was stirred at room temperature for 3 h. ER (100 ml) was added and the mixture was filtered and evaported. The residue in methanol (100 ml) was treated portionwise with sodium borohydride (1.69 g) under nitrogen. The solution was stirred for 3 h, treated with water (40 ml), and extracted with ER (3×200 ml). The dried extract was evaporated and the residue was twice purified by FCC eluting with ER-CX (3:1) to give the title compound as a yellow oil (6.8 g), t.l.c. (ER) Rf 0.3.

Intermediate 24

3-(Aminomethyl)-α-[[[6-(4-phenylbutoxy)hexyl](phenylmethyl)amino]methyl]-4-(phenylmethoxy)benzenemethanol Intermediate 23 (9.0 g) in THF (80 ml) was added dropwise to a suspension of lithium aluminium hydride (1.14 g) in THF (100 ml) at 0° under nitrogen. The mixture was refluxed for 28 h, cooled, treated cautiously with water (5 ml) and aqueous sodium hydroxide (2M; 5 ml), filtered, and evaporated. The residue was purified by FCC eluting with EA to give the title compound as a pale yellow oil (2.89 g), t.l.c. (EA) Rf 0.1.

Intermediate 25

N-[[5-[1-Hydroxy-2-[[6-(4-phenylbutoxy)hexyl](phenylmethyl)amino]ethyl]-2-(phenylmethoxy)phenyl]methyl]formamide A solution of Intermediate 24 (1.0 g) in n-butyl formate (10 ml) was refluxed for 1 h and evaporated. The residue in methanol (20 ml) was treated with potassium carbonate (0.5 g), and the suspension was stirred at room temperature for 1 h. Water (10 ml) was added and the emulsion was extracted with EA (3×50 ml). The dried extract was evaporated to give the title compound as a colourless oil (1.0 g), t.l.c. (System D 90:10:1) Rf 0.6

Intermediate 26

N-[[5-[1-Hydroxy-2-[[6-(4-phenylbutoxy)hexyl](phenylmethyl)amino]ethyl]-2-(phenylmethoxy)phenyl]methyl]methane sulphonamide Intermediate 24 (0.9 g) in pyridine (5 ml) was treated dropwise with methanesulphonyl chloride (0.195 g) and the solution was allowed to stand at room temperature for 18 h. Water (10 ml) was added and the emulsion was extracted with EA (2×50 ml). The dried extract was evaporated and the residue was purified by FCC eluting with EA to give the title compound as a pale yellow oil (0.5 g), t.l.c. (EA) RF 0.85.

Intermediate 27

[[5-[1-Hydroxy-2-[[6-(4-phenylbutoxy)hexyl](phenylmethyl)amino]ethyl]-2-(phenylmethoxy)phenyl]methyl]urea A solution of Intermediate 24 (0.7 g) and potassium cyanate (0.4 g) in hydrochloric acid (2M; 5 ml) and ethanol (15 ml) was refluxed for 3 h, treated with aqueous sodium bicarbonate (1M; 50 ml), and extracted with EA (2×100 ml). The dried extract was evaporated and the residue was purified by FCC eluting with EA to give the title compound as an oil (340 mg) which was used without further purification.

Intermediate 28

Ethyl N-[5-[1-hydroxy-2-[(phenylmethyl)[6-(3-phenylpropoxy)hexyl]amino]ethyl]-2-(phenylmethoxy)phenyl]carbamate A solution of ethyl N-[5-bromoacetyl-2-(phenylmethoxy)phenyl]carbamate (0.58 g), N-[6-(3-phenylpropoxy)hexyl]benzenemethanamine hydrobromide (0.66 g) and DEA (0.48 g) in dichloromethane (15 ml) was stirred at room temperature under nitrogen for 26 h. Dichloromethane (50 ml) was added, the solution washed successively with 2N hydrochloric acid (50 ml), water (50 ml), 8% sodium bicarbonate solution (50 ml), dried and evaporated in vacuo. The residual brown oil (1.02 g) in absolute ethanol (20 ml) at 0° was treated with sodium borohydride (0.15 g), and the mixture was allowed to warm up to room temperature and stirred under nitrogen for 18 h. 2N Hydrochloric acid (5 ml) was cautiously added, the mixture stirred at room temperature for 5 min and evaporated in vacuo. The residue was partitioned between 8% sodium bicarbonate solution (10 ml) and EA (20 ml) and the organic phase dried and evaporated in vacuo to give a yellow oil. Purification by FCC on triethylamine deactivated silica (40 g) eluting with ER-CX (7:3) gave the title compound as a colourless oil (0.84 g).

Found: C,75.0; H,7.9; N,4.5. $C_{40}H_{50}N_2O_5$ requires C,75.2; H,7.9; N,4.4%.

Intermediate 29

3-(Methylamino)-4-(phenylmethoxy)-α-[[(phenylmethyl)[6-(3-phenylpropoxy)hexyl]amino]methyl]benzenemethanol A solution of Intermediate 28 (0.50 g) in dry THF (10 ml) was added to a stirred suspension of lithium aluminium hydride (275 mg) in dry THF (5 ml) under nitrogen and stirring continued for a further 22 h. 2N Hydrochloric acid (3 ml) was cautiously added dropwise, the majority of the THF removed in vacuo at 40° and the residue partitioned between 2N hydrochloric acid (25 ml) and EA (25 ml). The aqueous phase was extracted with further EA (10 ml), the combined organic layers washed with 8% sodium bicarbonate solution (25 ml), dried and concentrated to afford a brown oil. This was purified by FCC on triethylamine deactivated silica (9385) eluting with ER/CX (2:3→1:1) to give the title compound as a pale yellow oil (169 mg), t.l.c. (Et$_3$N deactivated SiO$_2$, ER/CX 2:3) Rf 0.50.

Intermediate 30

3-[(4-Bromobutyl)oxy]-1-propyne

A mixture of 2-propyn-1-ol (10 g), 1,4-dibromobutane (60 ml), 50% aqueous sodium hydroxide (60 ml) and TAB (2 g) was stirred vigorously overnight. Water (250 ml) was added and the mixture was extracted with ether (2×200 ml). The organic extracts were dried and concentrated to a yellow oil which was purified by FCC eluting with H→H/ER (19:1) to give the title compound as a colourless oil (19.7 g), t.l.c. (H-ER 19:1) Rf 0.37.

Intermediate 31

1-[4-[3-[(4-Bromobutyl)oxy]-1-propynyl]phenyl]pyrrolidine

A mixture of 1-(4-iodophenyl)pyrrolidine (22.8 g), Intermediate 30 (16.0 g), BTPC (1.5 g) and copper (I) iodide (150 mg) in DEA (125 ml) and THF (125 ml) was stirred under nitrogen for 18 h. The dark mixture was treated with ER (250 ml), the precipitate was removed by filtration and the filtrate was concentrated to a black oil which was purified by FCC eluting with H→H/ER (9:1) to give the title compound as a pale yellow oil (3.0 g), t.l.c. (H-ER 9:1) Rf 0.24.

Intermediate 32

1-[4-[3-[(4-Bromobutyl)oxy]propyl]phenyl]pyrrolidine

Intermediate 31 (6.7 g) was hydrogenated over pre-reduced 10% PdO-C in ethanol/THF (1:1, 60 ml). The catalyst was removed by filtration through hyflo and the solvent was evaporated to leave the title compound as a pale brown semi-solid (6.2 g), t.l.c. (H-ER 9:1) Rf 0.27.

Intermediate 33

1-[4-[3-[4-(2-Methyl-1,3-dithian-2-yl)butoxy]propyl]phenyl]pyrrolidine n-Butyllithium (1.5M in H, 12 ml) was added over 5 min to a stirred solution of 2-methyl-1,3-dithiane (2.4 g) in dry THF (30 ml) at 70° under nitrogen. The yellow solution was then stirred at −30°→ −20° for 2 h, cooled to −78° and treated with a solution of Intermediate 32 (6.1 g) in THF (25 ml). The solution was stirred at room temperature overnight, the solvent was evaporated and the residue was purified by FCC eluting with H→H/ER (9:1) to give the title compound as a pale yellow oil (3.2 g), t.l.c. (H/ER 9:1) Rf 0.18.

Intermediate 34

6-[3-[4-(1-Pyrrolidinyl)phenyl]propoxy]-2-hexanone

A solution of Intermediate 33 (3.2 g) in THF (50 ml) was added to a stirred suspension of mercury (II) chloride (8.5 g) and calcium carbonate (3.2 g) in methanol/water (9:1, 50 ml) and the mixture was stirred at reflux for 1 h. The reaction was filtered through hyflo, the filtrate was concentrated in vacuo and the resulting oil was dissolved in chloroform (50 ml). The resulting precipitate was removed by filtration, the solvent was evaporated and the residue was purified by FCC eluting with H/ER (19:1→4:1) to give the title compound as a crystalline mass (1.4 g), m.p. 30°-31°.

Intermediate 35

α-[[Bis(phenylmethyl)amino]methyl]-3-(methoxymethyl)-4-(phenylmethoxy)benzenemethanol A solution of 2-bromo-1-[3-(methoxymethyl)-4-(phenylmethoxy)phenyl]ethanone (2.0 g), dibenzylamine (1.2 g) and DEA (0.8 g) in THF (30 ml) was allowed to stand at room temperature for 18 h, filtered and evaporated. The residual oil was dissolved in ethanol (20 ml) and treated portionwise with sodium borohydride (0.23 g), under nitrogen. The mixture was stirred at room temperature for 1 h, treated with methanol (20 ml), and evaporated. The residue was purified by FCC eluting with CX-ER (3:1) to give the title compound as an off-white solid (2.3 g), m.p. 52°–57°, t.l.c. (CX-ER 1:1) Rf 0.5

Intermediate 36

4-Hydroxy-3-(methoxymethyl)-α-[[(phenylmethyl)[6-(3-phenylpropoxy)hexyl]amino]methyl]benzenemethanol A solution of 2-bromo-1-[4-hydroxy-3-(methoxymethyl)phenyl]ethanone (700 mg), N-[6-(3-phenylpropoxy)hexyl]benzenemethanamine hydrobromide (1.1 g) and DEA (0.95 ml) in dichloromethane (10 ml) was kept at room temperature overnight. ER (50 ml) was added and the suspension was washed twice with water, brine, dried and concentrated to an oil which was dissolved in ethanol (20 ml) and treated with sodium (400 mg). The solution was stirred and refluxed refluxed overnight, water (30 ml) was added and the mixture was extracted with ER (3×25 ml). The organic extracts were washed with brine, dried and concentrated to a red oil which was purified by FCC eluting with System E (80:20:1→66:33:1) to give the title compound as an oil (250 mg), t.l.c. (System E 66:37:1) Rf 0.22.

Intermediate 37

[3-(Methoxymethyl)-4-(phenylmethoxy)]-α-[[(phenylmethyl)[6-[2-[4-(1-pyrrolidinyl)phenyl]ethoxy]hexyl]amino]methyl]benzenemethanol A solution of 2-bromo-1-[3-(methoxymethyl)-4-(phenylmethoxy)phenyl]ethanone (2 g), N-[6-[2-[4-(1-pyrrolidinyl)phenyl]ethoxy]hexyl]benzenemethanamine (2.12 g) and DEA (1.48 g) in THF (40 ml) was stirred under nitrogen at room temperature overnight. The resulting precipitate was removed by filtration, the solvent was evaporated and the residue, in methanol (50 ml), was cooled in an ice bath and treated portionwise with sodium borohydride (1.3 g). After 2 h, the solution was brought to room temperature and concentrated in vacuo to a yellow oil. The oil was partitioned between water (70 ml) and EA (70 ml), and the organic layer was washed with brine (70 ml), dried and concentrated. The resulting yellow oil was purified by FCC System B (90:10:1) to give the title compound as a yellow oil (2.0 g), t.l.c. (System C 80:20:2) Rf 0.45.

Intermediate 38

N,N-Diethyl-4-[4-[[6-[[2-hydroxy-2-[3-(methoxymethyl)-4phenylmethoxy)phenyl[ethyl](phenylmethyl)amino]hexyl]oxy]butyl]benzamide A mixture of 2-bromo-1-[3-(methoxymethyl)-4-(phenylmethoxy]phenyl]ethanone (1.6 g), N,N-diethyl-4-[4-[[6-[(phenylmethyl)amino]hexyl]oxy]butyl]benzamide (2.00 g), DEA (0.85 ml) and THF (50 ml) was kept at 23° for 4 h, filtered and evaporated in vacuo. A solution of the residue in methanol (30 ml) was cooled to 5° and sodium borohydride (0.4 g) added portionwise over 0.5 h. After a further 0.5 h at 5°, the solution was evaporated in vacuo and the oily residue partitioned between ER (100 ml) and water (50 ml). The organic phase was washed with 2N sodium carbonate solution (40 ml), dried and evaporated in vacuo. The residual gum was purified by FCC eluting with ER-CX (2:1) to afford the title compound as a colourless gum (1.97 g), t.l.c. Rf 0.2.

Intermediate 39

2-[3-Fluoro-4-(phenylmethoxy)phenyl]oxirane

Sodium borohydride (1.25 g) was added in portions to a stirred solution of 2-bromo-1-[3-fluoro-4-(phenylmethoxy)phenyl]ethanone (16.6 g) in dioxan (100 ml) and methanol (100 ml) at 0°. After 0.5 h a solution of sodium hydroxide (4.0 g) in water (20 ml) was added and the mixture stirred for a further 1 h at 0°. Water was added and the mixture extracted with EA. The extracts were dried and evaporated to give the title compound as a colourless oil (12.6 g) which partially solidified on standing, t.l.c. (PE-EA 6:4) Rf 0.40.

Intermediate 40

3-Fluoro-4-(phenylmethoxy)-α-[[N-(phenylmethyl)amino]methyl]benzenemethanol

Intermediate 39 (4.70 g) and benzylamine (30.93 g) were refluxed in methanol (10 ml) under a nitrogen atmosphere for 2 h. The solvent was removed under reduced pressure and the product was partially purified by FCC eluting with System A (90:10:1). The resulting oil precipitated a white solid which was dried at 55° C. under high vacuum to afford the title compound (2.8 g) m.p. 113°–113.5°.

Intermediate 41

3-Fluoro-α-[[[6-(2-phenylethoxy)hexyl](phenylmethyl)amino]methyl]-4-(phenylmethoxy)benzenemethanol A mixture of Intermediate 40 (1.75 g), [2-[(6-bromohexyl)oxy]ethyl]benzene (3 g), potassium carbonate (0.7 g) and sodium iodide (1.5 g) in acetonitrile (120 ml) was stirred and refluxed for 6 days. The solvent was evaporated and the residue partitioned between water, 5M sodium hydroxide (1 ml) and ER. The organic phase was dried and evaporated to leave a gum (4.3 g) which was purified by FCC eluting with PE-ER (12:1) to give the title compound as a colourless gum (2.2 g).

Found: C,76.9; H,8.0; N,2.9. $C_{30}H_{42}FNO_3$ requires C,77.8; H,7.6; N,2.5%.

Intermediate 42

3-Fluoro-α-[[[6-(2-phenylbutoxy)hexyl](phenylmethyl)amino]methyl]-4-(phenylmethoxy)benzenemethanol A mixture of Intermediate 40 (1.75 g), [4-[(6-bromohexyl)oxy]butyl]benzene (3 g), potassium carbonate (0.7 g) and sodium iodide (1.5 g) in acetonitrile (120 ml) was stirred and refluxed for 6 days. The solvent was evaporated and the residue partitioned between ER and water. The organic phase was dried and evaporated to leave a gum (4.2 g). This was purified by FCC eluting with PE-ER (2:1) to give the title compound as a colourless gum (2.6 g).

Found: C,78.0; H,8.2; N,2.4. $C_{38}H_{46}FNO_3$ requires C,78.2; H,8.0; N,2.4%.

Intermediate 43

N-[4-[2-[[6-[[2-(3-Hydroxyphenyl)-2-oxoethyl](phenylmethyl)amino]hexyl]oxy]ethyl]phenyl]acetamide A solution of N-[4-[2-[[6-[(phenylmethyl)amino]hexyl]oxy]ethyl]phenyl]acetamide (1 g), 2-bromo-1-(3-hydroxyphenyl)ethanone (0.61 g) and DEA (0.8 g) in dichloromethane (20 ml) was stirred under nitrogen for 18 h, diluted with water (20 ml), and extracted with dichloromethane (25 ml). The organic layer was washed with 8% sodium bicarbonate solution (20 ml), dried and evaporated in vacuo to give the title compound as a yellow oil (0.71 g).

Found: C,73.3; H,7.9; N,5.1. $C_{31}H_{38}N_2O_4.0.5H_2O$ requires C,72.8; H,7.7; N,5.4%.

Intermediate 44

N,N-Diethyl-4-[4-[[6-[[2-[3-fluoro-4-(phenylmethoxy)phenyl]-2-hydroxyethyl(phenylmethyl)amino]hexyl]oxy]butyl]benzamide A mixture of 3-fluoro-4-(phenylmethoxy)-α-[[(phenylmethyl)amino]methyl]benzenemethanol (0.9 g), 4-[4-[(6-bromohexyl)oxy]butyl]-N,N-diethylbenzamide (2.11 g), potassium carbonate (0.37 g) and sodium iodide (0.77 g) in acetonitrile (60 ml) was heated at reflux for 22 h, cooled and evaporated in vacuo. The residual gum was purified by FCC eluting with H-ER (1:1→1:2) to give the title compound as a colourless oil (1.64 g), t.l.c. (ER) Rf 0.68.

Intermediate 45

N,N-Diethyl-4-[4-[[6-[(phenylmethyl)amino]hexyl]oxy]butyl]benzamide

4-[4-[(6-Bromohexyl)oxy]butyl]-N,N-diethybenzamide (6.0 g) and benzylamine (9.36 g) were stirred under nitrogen at 120° for 30 mins. Excess benzylamine was removed by distillation under reduced pressure. The residual solid was dissolved in ethyl acetate (100 ml) and washed with 8% aqueous sodium bicarbonate (100 ml). The ethyl acetate solution was dried and evaporated to give a yellow oil which was purified by FCC eluting System B (95:5:1) to give the title compound as a yellow oil (4.88 g), t.l.c. (System B 95:5:1) Rf 0.15.

Example 1

3-Hydroxy-α$^6$-[[[1-methyl-6-(2-phenylethoxy)hexyl]amino]methyl]-2,6-pyridinedimethanol dihydrochloride A solution of Intermediate 2 (450 mg), 1N methanolic hydrogen chloride (3 ml) and water (0.03 ml) in methanol (15 ml) was stirred at 50° C. for 6 h then left at room temperature for 3 days. Additional acid (3 ml) and water (0.03 ml) were added and the solution was stirred at 50° C. for 18 h. Some of the methanol (~10 ml) was evaporated and ER (50 ml) was added, to yield a yellow oil. Repeated trituration of the oil with dry ER gave the title compound as a cream solid (300 mg) m.p. 105°–108°.

Analysis Found: C,56.89; H,7.43; N,5.64; Cl,14.26. $C_{23}H_{34}N_2O_4.2HCl.0.5H_2O$ requires C,57.02; H,7.70; N,5.78; Cl,14.63%.

Example 2

3-Hydroxy-$\alpha^6$-[[[6-(4-phenylbutoxy)hexyl]amino]methyl]-2,6-pyridinedimethanol dihydrobromide Intermediate 3 (1.5 g) was hydrolysed as in Example 5. Concentration of the EA extract gave a red oil which was purified by FCC eluting with System B (80:20:1) to give an oil 720 mg. A portion of this oil (300 mg) in methanol (5 ml) was treated with hydrobromic acid (1M in methanol, 1.5 ml). The solution was concentrated to an oil which was triturated with ER to give the title compound as a pale brown powder (390 mg), t.l.c. (System C 80:20:1) Rf 0.07

Example 3

3-Hydroxy-$\alpha^6$-[[[6-[3-[4-(1-piperidinyl)phenyl]propoxy]hexyl]amino]methyl]-2,6-pyridinedimethanol trihydrobromide A solution of Intermediate 7 (520 mg) and 2N hydrochloric acid (3 ml) in methanol (10 ml) and THF (5 ml) was left at room temperature for 2 days. The solvent was evaporated and the residue was dried by azeotroping with toluene. The resultant oil was purified by FCC eluting with System C (80:20:1) to give an oil (330 mg). A portion of this oil (270 mg) in methanol (5 ml) was treated with hydrobromic acid (1M in methanol, 2 ml), the solvent was evaporated and the residual oil was triturated with dry ER to give the title compound as a fawn powder (310 mg), t.l.c. (System C 80:20:1) Rf 0.10.

Analysis Found: C,44.20; H,6.40; N,5.30; Br,30.78. $C_{28}H_{43}N_3O_4.3HBr.2H_2O$ requires C,43.99; H,6.59; N,5.50; Br,31.36%.

Example 4

N-[4-[4-[[6-[[2-Hydroxy-2-[3-hydroxy-2-(hydroxymethyl)-6-pyridinyl]ethyl]amino]hexyl]oxy]butyl]phenyl]-butanesulphonamide Intermediate 8 (500 mg) was hydrolysed as in Example 5. Concentration of the EA extract gave a dark oil which was purified by FCC eluting with System C (80:20:1) followed by triburation with dry ER to give the title compound as a brown powder (70 mg), m.p. 55°–57°, t.l.c. (System C 80:20:1) Rf 0.07.

Example 5

3-Hydroxy-$\alpha^6$-[[[3-[(6-phenylhexyl)oxy]propyl]amino]methyl]-2,6-pyridinedimethanol Intermediate 9 (0.59 g) was stirred in a mixture of 2N hydrochloric acid (3.2 ml) and methanol (10 ml) for 20 h. The solvent was evaporated in vacuo, the residue treated with 8% sodium bicarbonate solution (150 ml) and extracted with EA (3×50 ml). The combined organic extracts were washed with brine (100 ml), dried and evaporated in vacuo to give an oil which on trituration with ER gave the title compound as a brown gum (0.3 g).

Assay Found: C,65.81; H,8.42; N,6.81. $C_{23}H_{34}N_2O_4.H_2O$ requires C,65.68; H,8.63; N,6.66%.

Example 6

3-Hydroxy-$\alpha^6$-[[[6-[[4-(4-fluorophenyl)-33-butylnyl]oxy]hexyl]amino]methyl]-2,6-pyridinedimethanol Intermediate 12 (0.78 g) was hydrolysed as in Example 5 (except for omission of the ER trituration) to give the title compound as a brown gum (0.65 g).

Assay Found: C,66.41; H,7.32; N,5.97. $C_{24}H_{31}FN_2O_4.0.25H_2O$ requires C,66.25; H,7.30; N,6.44%.

Example 7

$\alpha^6$-[[[6-[4-(4-Fluorophenyl)butoxy]hexyl]amino]methyl]-3-hydroxy-2,6-pyridinedimethanol A solution of Example 6 (0.26 g) in absolute ethanol (16 ml) was hydrogenated over pre-reduced 10% PdO-C (60 mg) in absolute ethanol (5 ml). The mixture was filtered through 'hyflo' and evaporated in vacuo to give an oil which on trituration with ER gave the title compound as a brown gum (0.13 g), t.l.c. (System C 39:10:1) Rf 0.09

Analysis Found: C,62.0; H,7.8; N,5.4. $C_{24}H_{35}FN_2O_4.1.5H_2O$ C,62.4; H,8.3; N,6.0%.

Example 8

3-Hydroxy-$\alpha^6$-[[[6-[4-(4-methylphenyl)butoxy]hexyl]amino]methyl]2,6-pyridinedimethanol Intermediate 13 (0.95 g) was hydrolysed as in Example 5. Concentration of the EA extract gave an oil (0.769 g) which was purified by FCC eluting with System B (80:20:1) to give the title compound as an orange oil (0.284 g), t.l.c. (System C 39:11:1) Rf 0.1.

Analysis Found: C,58.8; H,5.4; N,5.8. $C_{25}H_{38}N_2O_4$ requires C,58.9; H,5.3; N,5.5%.

Example 9

3-Hydroxy-$\alpha^1$-[[[6-[3-[4-(Methylthio)phenyl]propoxy]-hexyl]amino]methyl]-2,6-pyridinedimethanol, hydrobromide Intermediate 15 (0.73 g) was hydrolysed as in Example 5, concentration of the EA extract giving an oil (0.456 g). The oil (160 mg) in methanol (2 ml) was treated with hydrogen bromide in methanol (1M, 0.70 ml). After 5 min the solvent was evaporated and the residue was triturated with ER to give the title compound as a cream solid (138 mg) m.p. 61°–62°, t.l.c. (System C 39:11:1) Rf 0.1

Example 10

3-Hydroxy-$\alpha^6$-[[[6-[4-(4-hydroxy-3-methoxyphenyl)-butoxy]hexyl]amino]methyl]-2,6-pyridinedimethanol Intermediate 19 (1.50 g) in ethanol (25 ml) and THF (25 ml) was hydrogenated over pre-reduced 10% Pd-C (50% paste in water, 50 mg) and 5% Pt-C (150 mg). The reaction mixture was filtered (hyflo), the filtrate was evaporated and the residue (1.08 g) was purified by FCC eluting with System B (80:2:1) to give the title compound as an orange foam (98 mg), t.l.c. (System C 39:11:1) Rf 0.06.

Analysis Found: C,62.6; H,8.4; N,5.7. $C_{25}H_{38}N_2O_6.H_2O$ requires C,62.5; H,8.4; N,5.8%.

Example 11

N-[[4-[[6-[[2-Hydroxy-2-[3-hydroxy-2-(hydroxymethyl)pyridin-6-yl]ethyl]amino]hexyl]oxy]butyl]phenyl]methyl]pentanamide hydrobromide Intermediate 21 (0.31 g) was hydrogenated over pre-reduced 10% Pd-C (50% aqueous paste 50 mg) and 5% Pt-C (50 mg) in ethanol (20 ml). The reaction mixture was filtered (hyflo) and the filtrate was concentrated to give an oil (0.25 g) which was purified by FCC eluting with System B (80:20:1) to give an oil (0.12 g). The oil in methanol (2 ml) was treated with hydrogen bromide in methanol (1M; 0.46 ml) and after 5 min the solvent was evaporated. The residue was triturated with ER to give the title compound as a pink solid (89 mg) m.p. 83°, t.l.c. (System C 39:11:1) Rf 0.1.

Example 12

3-Hydroxy-$\alpha^6$-[[[6-[4-(4-methoxyphenyl)butoxy]hexyl]amino]methyl]-1,6-pyridinedimethanol A suspension of Intermediate 22 (1.7 g) and 2N hydrochloric acid (8 ml) in methanol (25 ml) was stirred at room temperature overnight under nitrogen. The resulting yellow solution was concentrated in vacuo, diluted with water (50 ml) and washed with ether (3×25 ml). The aqueous layer was neutralised with 5N sodium hydroxide and extracted with EA (3×50 ml). The organic extracts were washed with brine, dried and concentrated in vacuo to give the title compound as an orange gum (1.3 g), t.l.c. (System C 80:20:2) Rf 0.10.

A solution of the title compound (645 mg) and hydrobromic acid (1M solution in methanol, 2.9 ml) was concentrated in vacuo and the residual oil was triturated several times with dry ether to give the dihydrobromide of the title compound as a hygroscopic cream powder (710 mg).

Analysis Found: C,48.67; H,6.94; N,4.49. $C_{25}H_{38}N_2O_5.2HBr.0.6H_2O$ requires C,48.49; H,6.71; N,4.52%.

Water Analysis 1.73% w/w.

Example 13

N-[[2-Hydroxy-5-[1-hydroxy-2-[[6-(4-phenylbutoxy)hexyl]amino]ethyl]phenyl]methyl]formamide A solution of Intermediate 25 (0.325 g) in ethanol (20 ml) was hydrogenated over 10% Pd-C (0.1 g), filtered, and evaporated. The resulting oil was triturated with ER (25 ml) to give the title compound as a white solid (0.4 g) m.p. 76°-77°, t.l.c. (System D 90:10:1) Rf 0.2.

Example 14

N-[[2-Hydroxy-5-[1-hydroxy-2-[[6-(4-phenylbutoxy)hexyl]amino]ethyl]phenyl]methyl]methanesulphonamide, benzoate salt A solution of Intermediate 26 (0.5 g) in ethanol (20 ml) was hydrogenated over 10% Pd-C (0.1 g), filtered and evaporated. The residue was purified by FCC eluting with System A (90:10:1). The resulting colourless oil (0.36 g) in chloroform (10 ml) was treated with a solution of benzoic acid (0.13 g) in chloroform (10 ml) and the chloroform was removed by evaporation. The residue was triturated with ER (2×20 ml) to give the title compound as a waxy yellow solid (0.07 g), t.l.c. (System D 90:10:1) Rf 0.15.

Analysis Found: C,64.8; H,7.5; N,4.3. $C_{26}H_{40}N_2O_5S.C_7H_6O_2$ requires: C,64.5; H,7.7; N,4.6%.

Example 15

[[2-Hydroxy-5-[1-hydroxy-2-[[6-(4-phenylbutoxy)hexyl]amino]ethyl]phenyl]methyl]urea, hydrochloride A solution of Intermediate 27 (340 mg) in ethanol (20 ml) was hydrogenated over 10% Pd-C (0.15 g), filtered and evaporated. The residue was purified by FCC eluting with System A (90:10:1) to give the title compound as a yellow gum (0.19 g), t.l.c. (System D 90:10:1) Rf 0.15.

Analysis Found: C,59.4; H,8.0; N,7.7. $C_{26}H_{39}N_3O_4.HCl.2H_2O$ requires: C,59.0; H,8.4; N,7.9%.

Example 16

4-Hydroxy-3-(methylamino)-$\alpha$-[[[6-(3-phenylpropoxy)hexyl]amino]methyl]benzenemethanol dihydrochloride A solution of Intermediate 29 (200 mg) in absolute ethanol (15 ml) was hydrogenated over pre-reduced 10% PdO-C (50 mg). The catalyst was removed by filtration through hyflo, the filtrate treated with an excess of ethereal hydrogen chloride and then evaporated in vacuo at 40°. The residual yellow gum was triturated with dry ER to afford the title compound as a very hygroscopic fawn powder (112 mg) which softened ca. 90°, t.l.c. (System C 39:10:1) Rf 0.33.

Analysis Found: C,53.85; H,7.87; N,5.12. $C_{24}H_{36}N_2O_3.2HCl.3.25H_2O$ requires C,54.18; H,8.05; N,5.27%.

Example 17

Ethyl N-[2-hydroxy-5-[1-hydroxy-2-[[6-(3-phenylpropoxy)hexyl]amino]ethyl]phenyl]carbamate hydrochloride A solution of Intermediate 28 (0.32 g) in absolute ethanol (10 ml) was hydrogenated over 10% Pd-C (80 mg). The mixture was filtered through hyflo and the filtrate evaporated in vacuo to give a yellow oil which was treated with ethereal hydrogen chloride and triturated with ER to give the title compound as an off-white solid (0.17 g) m.p. 123.5°-125°.

Analysis Found: C,60.9; H,8.0; N,5.4; Cl,7.8. $C_{26}H_{38}N_2O_5.HCl.0.75H_2O$ requires C,61.4; H,8.0; N,5.5; Cl,7.0%

Example 18

4-Hydroxy-3-(methoxymethyl)-$\alpha$-[[[6-[3-phenylpropoxy]hexyl]amino]methyl]benzenemethanol Intermediate 36 (250 mg) was hydrogenated in ethanol (20 ml) over pre-reduced 10% PdO-C (50 % aqueous paste, 50mg). The catalyst was removed by filtration through hyflo and the ethanol was removed under vacuum. Purification by FCC eluting with System A (80:20:1) gave a semi-solid which was triturated with ER to give the title compound as a white solid (120 mg), m.p. 68°-70°, t.l.c. (System A 80:20:1) Rf 0.31.

Example 19

$\alpha$-[[[5-[2-(4-Fluorophenyl)ethoxy]pentyl]amino]methyl]-4-hydroxy-3-(methoxy methyl)benzenemethanol A solution of 2-bromo-1-[3-(methoxymethyl)-4-(phenylmethoxy)phenyl]ethanone (1.0 g), N-[5-(2-(4-fluorophenyl)ethoxy]pentyl]benzenemethanamine (0.91 g), and DEA (0.77 g) in THF (15 ml) was left at room temperature for 18 h, filtered and evaporated. The residue was hydrogenated over 10% Pd-C (0.5 g) and 5%

Pt-C (0.5 g), filtered and evaporated. The resulting oil was purified by FCC eluting with System C (80:20:1) to give the title compound as a white solid (0.58 g) m.p. 86°–87°, t.l.c. (System C 80:20:1) Rf 0.25.

Example 20

[4-Hydroxy-3-(methoxymethyl)]-α-[[[1-methyl-5-[3-[4-(1-pyrrolidinyl)phenyl]propoxy]pentyl]amino]methyl]-benzenemethanol, (E)-2-butenedioate (salt) (2:1)

A mixture Intermediate 35 (0.47 g) and Intermediate 34 (0.30 g) in absolute ethanol (25 ml) and THF (5 ml) was hydrogenated over a pre-reduced 10% PdO-C (0.5 g, 50% paste in H₂O) and 5% PtO-C (0.25 g) catalyst mixture. The catalyst was removed by filtration through 'hyflo' and the solvent removed in vacuo at 40° to yield a product which was purified by FCC eluting with System C (39:10:1). Concentration of the eluant afforded the title compound free base as a viscous pale yellow oil (165 mg), which was dissolved in methanol (2 ml), the solution treated with fumaric acid (21 mg) in methanol (2 ml) and the solvent removed in vacuo at 40°. Trituration with ER afforded the title compound as a white powder (140 mg) m.p. 132°–135°, t.l.c. (System C 39:10:1) Rf 0.32.

Example 21

4-Hydroxy-3-(methoxymethyl)-α-[[[6-[2-(4-methoxyphenyl)ethoxy]hexyl]amino]methyl]benzenemethanol A solution of 2-bromo-1-[3-(methoxymethyl)-4-(phenylmethoxy)phenyl]ethanone (1.38 g), N-[6-[2-(4-methoxyphenyl)ethoxy]hexyl]benzenemethanamine (1.35 g) and DEA (1.02 g) in THF (21 ml) was allowed to stand under nitrogen for 20 h. The mixture was filtered and the filtrate evaporated in vacuo to give an oil, a solution of which in ethanol (35 ml) was hydrogenated over pre-reduced 10% PdO-C (50% aqueous, 500 mg) and 5% PtO-C (400 mg). The mixture was filtered through hyflo and evaporated in vacuo to give an oil. Purification by FCC eluting with System B (900:100:5) gave the title compound as a cream solid (0.82 g) m.p. 97.5°–98.5°.

Analysis Found: C,69.78; H,8.78; N,3.18. C₂₅H₃₇NO₅ requires C,69.58; H,8.64; N,3.25%.

Example 22

[4-Hydroxy-3-(methoxymethyl)]-α-[[[6-[2-[4-(1-pyrrolidinyl)phenyl]ethoxy]hexyl]amino]methyl]benzenemethanol Intermediate 37 (1.91 g) was hydrogenated over pre-reduced 10% PdO-C (50% aqueous paste, 500 mg) in ethanol (25 ml) and THF (3 ml). The catalyst was removed by filtration through hyflo and the ethanol was evaporated to give a white gum (1.2 g) which was triturated with ER to give the title compound as a white solid (1.0 g) m.p. 92°–95°.

Analysis Found: C,71.37; H,9.24; N,5.88. C₂₈H₄₂N₂O₄ requires C,71.45; H,9.00; N,5.95%.

Example 23

N,N-Diethyl 4-[4-[[6-[[2-hydroxy-2-[4-hydroxy-3-(methoxymethyl)phenyl]ethyl]amino]hexyl]oxy]butyl]benzamide A solution of Intermediate 38 (1.92 g) in ethanol (50 ml) was added to a pre-reduced suspension of 10% Pd-C (0.7 g) in ethanol (20 ml) and hydrogenated. The catalyst was removed by filtration through hyflo and the filtrate evaporated in vacuo. The residue was co-evaporated with EA to afford the title compound as a yellow gum (1.31 g), t.l.c. (System C 39:10:1) Rf 0.28.

Analysis Found: C,70.1; H,9.3; N,5.4. C₃₁H₄₈N₂O₅.0.2C₄H₈O₂ requires C,69.9; H,9.15; N,5.13%.

Example 24

3-Fluoro-4-hydroxy-α-[[[6-(2-phenylethoxy)hexyl]amino]methyl]benzenemethanol, hemifumarate (salt)

A solution of Intermediate 41 (2.1 g) in dry THF (100 ml) was hydrogenated over 10% Pd-C. Catalyst and solvent were removed to leave a colourless gum (1.5 g) which was dissolved in methanol (10 ml) and heated with a solution of fumaric acid (230 mg) in methanol (10 ml). EA (120 ml) was added and the solution concentrated to give the title compound (0.8 g) m.p. 145°–146°.

Found: C,66.2; H,7.3; N,3.2. C₂₂H₃₀FNO₃.0.5C₄H₄O₄ requires C,66.5; H,7.4; N,3.2%.

Example 25

3-Fluoro-4-hydroxy-α-[[[6-(4-phenylbutoxy)hexyl]amino]methyl]benzenemethanol, hemifumarate (salt)

A solution of Intermediate 42 (2.2 g) in dry THF (50 ml) was hydrogenated over 10% Pd-C (100 mg). Catalyst and solvent were removed to leave a gum (1.6 g) which was dissolved in ER and treated with a solution of fumaric acid (180 mg) in methanol (3 ml). The resultant precipitate was dissolved by the addition of more methanol (~25 ml). EA (75 ml) was added and the solution concentrated to give the title compound (1.1 g) m.p. 140°–142°.

Found: C,67.8; H,7.8; N,3.0. C₂₄H₃₄FNO₃.0.5C₄H₄O₄ requires C,67.7; H,7.9; N,3.0%.

Example 26

N-[4-[2-[[6-[[2-Hydroxy-2-(3-hydroxyphenyl)ethyl]amino]hexyl]oxy]ethyl]phenyl]acetamide hydrochloride A solution of Intermediate 43 (0.7 g) in absolute ethanol (30 ml) was hydrogenated over a pre-reduced mixture of 10% Pd-C (300 mg) and 5% Pt-C (300 mg) catalysts in absolute ethanol (10 ml). The mixture was filtered through hyflo and evaporated in vacuo to give a light brown oil. Purification by FCC on triethylamine deactivated silica (Merck 9385) eluting with EA-Methanol (7:1) gave a colourless oil (0.51 g). Treatment with ethereal hydrogen chloride followed by evaporation in vacuo gave the title compound as a cream foam (0.29 g), t.l.c. triethylamine deactivated silica (EA-Methanol 7:1) Rf 0.17.

Found: C,61.0; H,8.1; N,5.65. C₂₄H₃₄N₂O₄.1.125HCl.H₂O requires C,60.9; H,7.9; N,5.9%.

Example 27

3-Fluoro-4-hydroxy-α-[[[6-[3-[4-(methylthio)phenyl]propoxy]hexyl]amino]methyl]benzenemethanol Intermediate 14 (1.4 g) was added to a solution of α-(aminomethyl)-3-fluoro-4-hydroxybenzenemethanol (0.7 g), and DEA (1.0 g) in DMF (20 ml) at 70°. The mixture was heated at 70°–80° for 2 h evaporated under reduced pressure and the residue was purified by FCC eluting with System C (80:20:1) to give a colourless gum. Trituration of the gum with ER (20 ml) gave the title compound as a white solid (0.30 g) m.p. 66°–67°, t.l.c. (System C 80:20:1) Rf 0.3.

Example 28

N,N-Diethyl-4-[4-[[6-[[2-(3-fluoro-4-hydroxyphenyl)-2-hydroxyethyl]amino]hexyl]oxy]butyl]benzamide, (E)-butenedioate salt (2:1)

A solution of Intermediate 44 (1.59 g) in ethanol (30 ml) was added to a suspension of pre-reduced 10% Pd-C (50% aqueous paste, 0.25 g) in ethanol (25 ml) and hydrogenated. The catalyst was removed by filtration through hyflo and the filtrate evaporated in vacuo. The residual gum in methanol (20 ml) was treated with fumaric acid (135 mg), evaporated in vacuo and triturated with dry ER (×2). The crystalline residue was recrystallised from isopropanol to afford the title compound (770 mg) m.p. 154°–156°.

Analysis Found: C,66.35; H,8.3; N,4.8. $C_{31}H_{45}FN_2O_6$ requires C,66.4; H,8.1; N,5.0%.

Example 29

N,N-Diethyl-4-[4-[[6-[2-hydroxy-2-(3-hydroxyphenyl)ethyl]amino]hexyl]oxy]butyl]benzamide, (E)-butenedioate salt (2:1)

A solution of 1-[3-hydroxyphenyl]ethanone (0.98 g), Intermediate 45 (2.0 g) and DEA (1.18 g) in THF (40 ml) was allowed to stand under nitrogen for 23 h. The mixture was filtered and the filtrate evaporated in vacuo to give a brown oil, a solution of which in absolute ethanol (50 ml) was hydrogenated over pre-reduced 10% PdO-C (50% aqueous paste, 500 mg) and 5% PtO-C (400 mg) in absolute ethanol (10 ml). The mixture was filtered through hyflo and evaporated in vacuo to give an oil. Purification by FCC eluting with System B (92:8:1) gave a brown oil (1.53 g). This was dissolved in methanol (10 ml) and treated with fumaric acid (0.14 g), evaporated in vacuo and triturated with ether to give the title compound as a cream foam (0.94 g), t.l.c. (System C 40:10:1) Rf 0.24.

Analysis Found: C,66.8; H,8.5; N,4.9. $C_{29}H_{44}N_2O_4$·0.5 $C_4H_4O_4$·$H_2O$ requires C,66.4; H,8.6; N,5.0%.

The following are examples of suitable formulations of compounds of the invention. The term 'active ingredient' is used herein to represent a compound of the invention.

| Tablets (Direct Compresssion) | mg/tablet |
|---|---|
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

| Metered Dose Pressurised Aerosol (Suspension Aerosol) | | |
|---|---|---|
| | mg/metered dose | Per can |
| Active ingredient micronised | 0.100 | 26.40 mg |
| Oleic Acid BP | 0.100 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluromethane is pressure filled into the cans through the valves.

| Inhalation Cartridges | mg/cartridge |
|---|---|
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of formula (I).

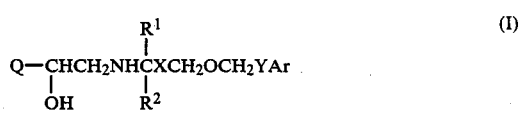

wherein

Ar represents a phenyl group optionally substituted by one or more substituents selected from halogen atoms, or the groups $C_{1-6}$alkyl, nitro, —$(CH_2)_qR$, [where R is hydroxy, $C_{1-6}$ alkoxy, —$NR^3R^4$ (where $R^3$ and $R^4$ each represents a hydrogen atom, or a $C_{1-4}$ alkyl group, or —$NR^3R^4$ forms a saturated heterocyclic amino group which has 5–7 ring members and optionally contains in the ring one or more atoms selected from —O— or —S— or a group —NH— or —N($CH_3$)—), —$NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or —$NR^3R^4$ group), —$NR^5SO_2R^7$ (where $R^7$ represents a $C_{1-4}$ alkyl, phenyl or —$NR^3R^4$ group), —$COR^8$ (where $R^8$ represents hydroxy, $C_{1-4}$ alkoxy or —$NR^3R^4$), —$SR^9$ (where $R^9$ is a hydrogen atom, or a $C_{1-4}$ alkyl or phenyl group), —$SOR^9$, —$SO_2R^9$, or —CN, and q represents an integer from 0 to 3], or —$O(CH_2)_tR^{10}$ [where $R^{10}$ represents a hydroxy or $C_{1-4}$ alkoxy group, and t is an integer 2 or 3], or Ar is a phenyl group substituted by an alkylenedioxy group of formula —$O(CH_2)_pO$—, where p represents an integer 1 or 2;

$R^1$ and $R^2$ each represents a hydrogen atom or a $C_{1-3}$ alkyl group with the proviso that the sum total of carbon atoms in $R^1$ and $R^2$ is not more than 4;

X represents a bond or a $C_{1-7}$ alkylene, $C_{2-7}$ alkenylene or $C_{2-7}$ alkynylene chain and Y represents a bond or a $C_{1-6}$ alkylene, $C_{2-6}$ alkenylene or $C_{2-6}$ alkynylene chain with the proviso that the sum total of carbon atoms in X and Y is 2-10;

Q represents the group

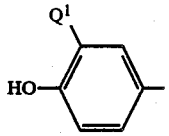

[where $Q^1$ represents the group —$CH_2R^{23}$ (where $R^{23}$ represents $C_{1-3}$ alkoxy, methanesulphonyl or cyano), or the group —$CH_2NHR^{11}$ (where $R^{11}$ represents $R^{12}CO$—, $R^{12}NHCO$—, $R^{12}R^{13}NSO_2$— or $R^{14}SO_2$—, where $R^{12}$ and $R^{13}$ each represent a hydrogen atom or a $C_{1-3}$ alkyl group, and $R^{14}$ represents a $C_{1-3}$ alkyl group), or the group —$NR^{15}R^{16}$ (where $R^{15}$ represents a hydrogen atom or a $C_{1-4}$alkyl group, and $R^{16}$ represents a hydrogen atom or a $C_{1-4}$alkyl group or, when $R^{15}$ is a hydrogen atom, $R^{16}$ also represents a $C_{1-4}$ alkoxycarbonyl group)], or Q represents the group

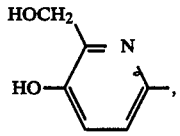

or Q represents a phenyl group substituted by a hydroxy group and optionally also by a halogen atom;

or a physiologically acceptable salt or solvate thereof.

2. A compound according to claim 1 in which the sum total of carbon atoms in the chains X and Y is 5, 6 or 7.

3. A compound according to claim 1 in which X represents —$(CH_2)_3$— or —$(CH_2)_4$—, and Y represents —$CH_2$—, —$(CH_2)_2$— or —$(CH_2)_3$—.

4. A compound according to claim 1 in which $R^1$ is a hydrogen atom and $R^2$ is a hydrogen atom or a methyl group.

5. A compound according to claim 1 in which Q represents the group

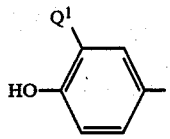

and $Q^1$ represents: methoxymethyl; —$CH_2NHR^{11}$ where $R^{11}$ is HCO—, $CH_3CO$—, $NH_2CO$—, $NH_2SO_2$— or $CH_3SO_2$—; or —$NR^{15}R^{16}$ where $R^{15}$ represents a hydrogen atom and $R^{16}$ represents a methyl group.

6. A compound according to claim 1 in which Q represents

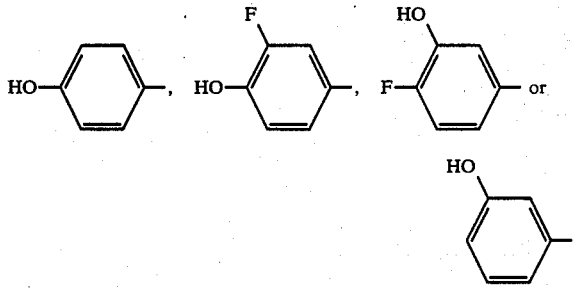

7. A compound according to claim 1 in which Ar is a phenyl group or a phenyl group substituted by chlorine, bromine, iodine, fluorine, methyl, ethyl, methoxy, ethoxy, —$(CH_2)_qR$, —$NO_2$, —$O(CH_2)_2OH$, —$O(CH_2)_3OH$, —$O(CH_2)_2OCH_3$, or —$O(CH_2)_2OCH_2CH_3$.

8. A compound according to claim 1 in which Ar is phenyl, or phenyl substituted by a halogen atom, or by a group selected from $C_{1-4}$ alkyl, $C_{1-4}$ alkoxy, a 5-7 membered heterocyclic amino group, —$SR^9$ (where $R^9$ is $C_{1-4}$ alkyl), —$CONR^3R^4$ (where $R^3$ and $R^4$ represent $C_{1-4}$ alkyl), —$NHSO_2R^7$ (where $R^7$ is $C_{1-4}$ alkyl), or —$(CH_2)_qNHCOR^6$ (where q is zero or 1, and $R^6$ is $C_{1-4}$ alkyl), or Ar represents phenyl substituted by methoxy and hydroxy.

9. A pharmaceutical composition which comprises an effective amount of at least one compound of general formula (I) as defined in claim 1 or a physiologically acceptable salt of solvate thereof, together with a physiologically acceptable carrier or diluent.

* * * * *